US011935655B2

(12) United States Patent
Ullaskrishnan et al.

(10) Patent No.: US 11,935,655 B2
(45) Date of Patent: Mar. 19, 2024

(54) SCALABLE DEPLOYMENT OF ONTOLOGY-BASED DECISION TREES FOR CLINICAL DECISION SUPPORT AND AUTOMATED CLINICAL WORKFLOWS

(71) Applicant: Siemens Healthcare Diagnostics Inc., Tarrytown, NY (US)

(72) Inventors: Poikavila Ullaskrishnan, Lebanon, NH (US); Ralf Krumtünger, Erlangen (DE); Teodora-Vanessa Liliac, Brasov (RO); Larisa Micu, Brasov (RO); Ingo Schmuecking, Yardley, PA (US); Puneet Sharma, Princeton Junction, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/812,476

(22) Filed: Jul. 14, 2022

(65) Prior Publication Data
US 2024/0021305 A1 Jan. 18, 2024

(51) Int. Cl.
*G16H 50/20* (2018.01)
*G06F 16/31* (2019.01)
*G06F 16/36* (2019.01)
*G16H 10/60* (2018.01)

(52) U.S. Cl.
CPC .......... *G16H 50/20* (2018.01); *G06F 16/322* (2019.01); *G06F 16/367* (2019.01); *G16H 10/60* (2018.01)

(58) Field of Classification Search
CPC ...... G16H 50/20; G16H 10/60; G06F 16/322; G06F 16/367
See application file for complete search history.

(56) References Cited

U.S. PATENT DOCUMENTS

| 9,183,244 | B2 * | 11/2015 | Bullis | ................. H04L 63/0227 |
| 2008/0201280 | A1 * | 8/2008 | Martin | .................. G06N 20/00 706/45 |
| 2011/0071850 | A1 * | 3/2011 | Nuthi | ...................... G16Z 99/00 705/3 |
| 2016/0371446 | A1 * | 12/2016 | Otin | ....................... G16H 40/63 |
| 2018/0240552 | A1 * | 8/2018 | Tuyl | ........................ G16H 50/20 |
| 2020/0349641 | A1 * | 11/2020 | Fidanza | ................. G06N 20/00 |
| 2022/0013218 | A1 | 1/2022 | Cousin | |
| 2022/0035998 | A1 | 2/2022 | Galitsky | |

OTHER PUBLICATIONS

Du et al., "A Knowledge Graph of Combined Drug Therapies Using Semantic Predications From Biomedical Literature: Algorithm Development", JMIR Medical Informatics, 2020, vol. 8, 1-12 pgs.
(Continued)

*Primary Examiner* — Etienne P Leroux (57) ABSTRACT

Systems and methods for determining an evaluation of one or more patients is provided. User input for evaluating one or more patients is received. A commit bundle is retrieved from a commit database. An evaluation of the one or more patients is determined based on the user input using a medical ontology configured with the retrieved commit bundle. The medical ontology is separate from the commit database. Results of the evaluation of the one or more patients are output.

20 Claims, 5 Drawing Sheets

(56) References Cited

OTHER PUBLICATIONS

Longxiang et al., "Semantic Health Knowledge Graph: Semantic Integration of Heterogeneous Medical Knowledge and Services", BioMed Research International, 2017, 12 pgs.
Huang et al., "Constructing Knowledge Graphs of Depression", Health Information Science, International Conference on Health Information Science, Lecture Notes in Computer Science, 2017, 12 pgs.
"Organizational Case Studies, Decision Support with SNOMED", retrieved from https://confluence.ihtsdotools.org/display/DOCCDS/Organizational+Case+Studies, 2020, 1 pg.
Lee et al., "Literature review of SNOMED CT use", Journal of the American Medical Informatics Association, 2014, vol. 21, pp. e11-e19.
"Snomed Ct Compositional Grammar", retrieved from https://confluence.ihtsdotools.org/display/SLPG/SNOMED/+CT+Compositional+Grammar, 2020, 1 pg.
Kilicoglu et al., "Broad-coverage biomedical relation extraction with SemRep", BMC Bioinformatics, 2020, vol. 21, 1-28 pgs.
"Hermit Reasoner", retrieved from https://protegewiki.stanford.edu/wiki/HermiT, 2013, 2 pgs.
"Protege OWL Environment", retrieved from http://protegeproject.github.io/protege/getting-started, 2011, 7 pgs.
"Corrigendum to 2017 ESC/EACTS Guidelines for the management of valvular heart disease", European Heart Journal, 2018, vol. 39, p. 1980.
"Snomed OWL Toolkit", retrieved from https://github.com/IHTSDO/snomed-owl-toolkit, 2020, 5 pgs.
"SNOMED CT to ICD-10-CM Map", retrieved from https://www.nlm.nih.gov/research/umls/mapping_projects/snomedct_to_icd10cm.html, 2019, 1 pg.
Haeusler et al., "ChronoGraph: A Versioned TinkerPop Graph Database", Data Management Technologies and Applications, Data 2017, vol. 814, pp. 237-260.
Schandl, "Replication and Versioning of Partial RDF Graphs", The Semantic Web: Research and Applications, ESWC 2010, vol. 6088, pp. 31-45.
U.S. Appl. No. 17/655,001, "System and Methods for Knowledge Representation and Reasoning in Clinical Procedures", filed Mar. 16, 2022, 44 pgs.
International Search Report dated Aug. 21, 2023 in corresponding International Patent Application No. PCT/US2023/021148.
Maran; "QsarDB—not just open data, but also open predictive models in chemistry and related Science"; pp. 1-17; Research Data Aliance; Web. Aug. 11, 2017; URL:https://www.rd-allance.org/sites/default/2017-11-08-UMARAN-RDA-ESTScl-ToLLaaksonen.pdfttp://yada yada.
Bagherjeiran et al:; "Graph-Based Methods for Orbit Classification"; pp. 1-14; Lawrence Livermore National Laboratory. Web; Mar. 10, 2005; URL: https://computing.llnl.gov.default/files/21508.pdf.

* cited by examiner

302 → Edge: 709044004 | Chronic kidney disease (disorder) → 2667000 | Absent (qualifier value)

*If*

304 {
Edge: 431855005 | Chronic kidney disease stage 1 (disorder) → 2667000 | Absent (qualifier value)
*AND*
Edge: 431856006 | Chronic kidney disease stage 2 (disorder) → 2667000 | Absent (qualifier value)
*AND*
Edge: 433144002 | Chronic kidney disease stage 3 (disorder) → 2667000 | Absent (qualifier value)
*AND*
Edge: 431857002 | Chronic kidney disease stage 4 (disorder) → 2667000 | Absent (qualifier value)
*AND*
Edge: 433146000 | Chronic kidney disease stage 5 (disorder) → 2667000 | Absent (qualifier value)
*AND*

306 {
(
Edge: 262300005 | With glomerular filtration rate → 2667000 | Absent (qualifier value)
*OR*
Vertex: 262300005 | With glomerular filtration rate → 276138003 | Greater-than-or-equal symbol >= (qualifier value) | → 90
)

SCALABLE DEPLOYMENT OF ONTOLOGY-BASED DECISION TREES FOR CLINICAL DECISION SUPPORT AND AUTOMATED CLINICAL WORKFLOWS

TECHNICAL FIELD

The present invention relates generally to ontology-based clinical decision trees, and in particular to scalable deployment of ontology-based clinical decision trees for clinical decision support and automated clinical workflows.

BACKGROUND

Clinical decision trees are used for a variety of different clinical applications, such as, e.g., for clinical decision support or for automated clinical workflows. Often times, there is a need to update clinical decision trees to reflect state-of-the-art clinical knowledge and capabilities of medical devices. Conventional clinical decision trees are implemented using complex if-else statements that are not scalable. Such conventional clinical decision trees must be updated by expert software developers to write, view, and modify clinical rules and redeploy the updated ontology and, as such, are not easily scalable or maintainable. In addition, such conventional clinical decision trees may be deployed at clinical sites that have their own operating procedures, clinical rules, update cycles, and implementation and testing protocols, further complicating the updating of such conventional clinical decision trees.

BRIEF SUMMARY OF THE INVENTION

In accordance with one or more embodiments, systems and methods for determining an evaluation of one or more patients is provided. User input for evaluating one or more patients is received. A commit bundle is retrieved from a commit database. An evaluation of the one or more patients is determined based on the user input using a medical ontology configured with the retrieved commit bundle. The medical ontology is separate from the commit database. Results of the evaluation of the one or more patients are output.

In one embodiment, another commit bundle is retrieved from the commit database. User input is received for generating a new commit bundle based on the other commit bundle. The user input for generating the new commit bundle may be received from a non-developer end user. The new commit bundle is stored in the commit database.

In one embodiment, the commit database comprises a plurality of commit bundles representing different versions of rules of a decision tree. The commit bundle may comprise a commit representing rules of a decision tree and provenance metadata associated with the commit. The commit comprises a set of equations of edge properties and/or vertex properties. The set of equations of edge properties and/or vertex properties define modifications relative to a prior commit of a prior commit bundle. The set of equations of edge properties are based on a presence or absence of one or more edges in the medical ontology. The set of equations of vertex properties are based on values of properties associated with one or more vertices.

These and other advantages of the invention will be apparent to those of ordinary skill in the art by reference to the following detailed description and the accompanying drawings.

DETAILED DESCRIPTION

The present invention generally relates to methods and systems for scalable and maintainable deployment of ontology-based clinical decision trees for clinical decision support and automated clinical workflows. Generally, a clinical decision tree can be linearized into a set of clinical rules, where the outcome is the content of the leaf node and the conditions along the path form a conjunction in an if-clause.

Conventional clinical decision trees are not scalable and must be updated by expert software developers. In one example, such conventional clinical decision trees may be implemented by the systems and methods disclosed in U.S. Patent Application Publication No. 2022/0310260, filed Mar. 16, 2022, the disclosure of which is incorporated herein by reference in its entirety.

Embodiments described herein provide for non-expert end user maintenance of ontology-based clinical decision trees by enabling one or more end users to write, view, modify, and test the clinical rules and redeploy the updated ontology. In one embodiment multiple end users may write, view, modify, and test different branches of the clinical decision trees in parallel. Examples of such end users could be trained users from customers which have the knowledge graphs implemented, service engineers, clinical application specialists, or other non-developer users. Using a rule editor/viewer, the end users are not required to have developer experience in knowledge graph technologies. Non-expert end user maintenance is enabled by storing the clinical rules in a database separate from the medical ontology to allow the clinical rules to be easily visualized and modified by the non-expert end users, as well as by providing versioning control of the clinical rules to enable the non-expert end users to update the clinical rules by retrieving and modifying prior versions of the clinical rules. Such clinical rules are implemented herein as commit bundles. Advantageously, ontology-based clinical decision trees implemented in accordance with embodiments described herein may be updated by non-expert end users and are therefore easily scalable and maintainable.

Figure 1:
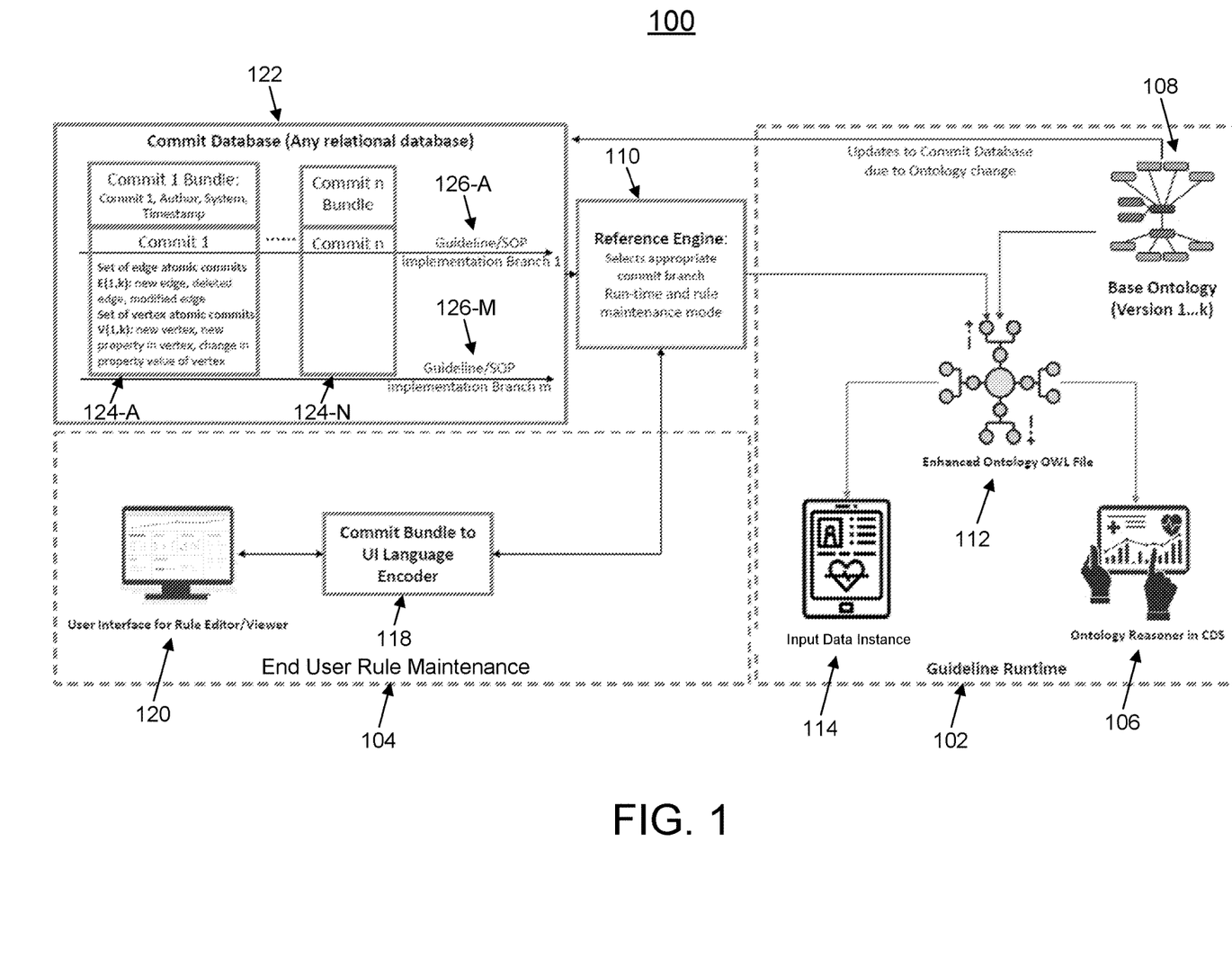
FIG. 1 shows a workflow for runtime and maintenance of ontology-based decision trees, in accordance with one or more embodiments.

FIG. 1 shows a workflow 100 for runtime and maintenance of ontology-based decision trees, in accordance with one or more embodiments. Workflow 100 comprises a guideline runtime stage 102 and an end user rule maintenance stage 104. During guideline runtime stage 102, one or more patients are evaluated using a medical ontology configured with a commit representing rules of a clinical decision tree. During end user rule maintenance stage 104, the clinical rules of the clinical decision tree are updated by generating a new commit. Guideline runtime stage 102 may be performed before, after, or simultaneously with end user rule maintenance stage 104. FIG. 1 will be described together with respect FIGS. 2 and 4.

Figure 2:
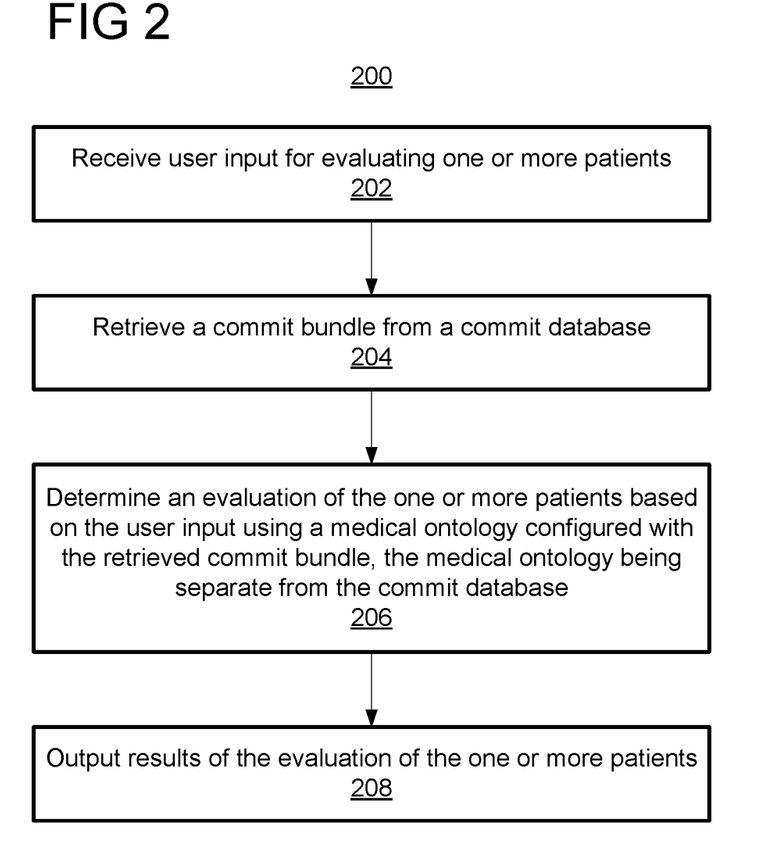
FIG. 2 shows a method for evaluating one or more patients using a medical ontology configured with a commit representing rules of a clinical decision tree, in accordance with one or more embodiments.

FIG. 2 shows a method 200 for evaluating one or more patients using a medical ontology configured with a commit representing rules of a clinical decision tree, in accordance with one or more embodiments. Method 200 is performed during a runtime stage for evaluating the one or more patients, such as, e.g., during guideline runtime stage 102 of FIG. 1. The steps of method 200 may be performed by one or more suitable computing devices, such as, e.g., computer 502 of FIG. 5.

At step 202 of FIG. 2, user input for evaluating one or more patients is received. The user input may be any suitable type of input from a user for evaluating the one or more patients. For example, the user input may be the automatic protocol selection in image acquisition devices, a follow-up procedure in a clinical workflow that is defined by clinical guidelines (e.g., another troponin test is needed or a CT scan is needed), etc. The user input may be received from a computing device (e.g., computer 502 of FIG. 5) that a user is interacting with, e.g., via mouse, trackpad, keyboard, touchscreen, or any other suitable input device of the computing device. In one example, as shown in guideline runtime stage 102 of FIG. 1, user input may be received from a user interacting with ontology reasoner 106 in a clinical decision support (CDS) system.

At step 204 of FIG. 2, in response to receiving the user input, a commit bundle is retrieved from a commit database. In one example, as shown in guideline runtime stage 102 of FIG. 1, a commit bundle 124-A, . . . , 124-N (collectively referred to as commit bundles 124) is selected and retrieved from commit database 122 by reference engine 110. Commit database 122 may be any suitable relational database for storing the commit bundles, such as, e.g., a structure query language (SQL) database. Each commit bundle 124 comprises a commit, as well as provenance metadata associated with the commit, such as, e.g., author, system, timestamp, unique identifier, etc. As used herein, a commit refers to one or more clinical rules representing a clinical decision tree for querying base ontology 108. Base ontology 108 comprises versions 1, . . . , k reflecting updates as commit database 122 is updated.

As shown in guideline runtime stage 102 of FIG. 1, commit database 122 comprises one or more branches 126-A, . . . , 126-M (collectively referred to herein as branches 126) each comprising one or more commit bundles 124. Each branch 126 represents an implementation of a clinical decision tree for, e.g., different clinical guidelines, different standard operating procedures (SOPs), etc. Commit bundles 124 of each respective branch 126 are associated with different versions acquired at different points in time and may be represented, e.g., chronologically by timestamp (or ordered by any other metadata) on the respective branch 126. Reference engine 110 selects an appropriate branch 126 and retrieves a (e.g., most recent) commit bundle 124 of the selected branch 126.

Each commit comprises a set of equations of edge properties and/or vertex properties of a medical ontology to define modifications of the clinical decision tree. The set of equations may be derived from rules of guidelines as defined by, e.g., clinical literature. Such modifications are defined relative to a prior commit of a prior commit bundle (e.g., an immediately prior commit bundle) in the selected branch 126. For example, commit n bundle 124-N defines modifications of the clinical decision tree relative to commit (n−1) bundle (not shown in FIG. 1). In one embodiment, the equations of edge properties are based on the Boolean presence or absence of one or more edges between specific vertices of the medical ontology and the equations of vertex properties are based on specific values of properties associated with one or more vertices of the medical ontology. The modifications defined by the commit may comprise atomic additions, deletions, and/or modifications of edges and/or vertices. For example, the commit may comprise atomic modifications of edges, such as, e.g., defining a new edge, deleting an edge, modifying an edge, etc., and atomic modifications of vertices, such as, e.g., defining a new vertex, defining a new property in a vertex, changing property values of a vertex, etc.

Figure 3:
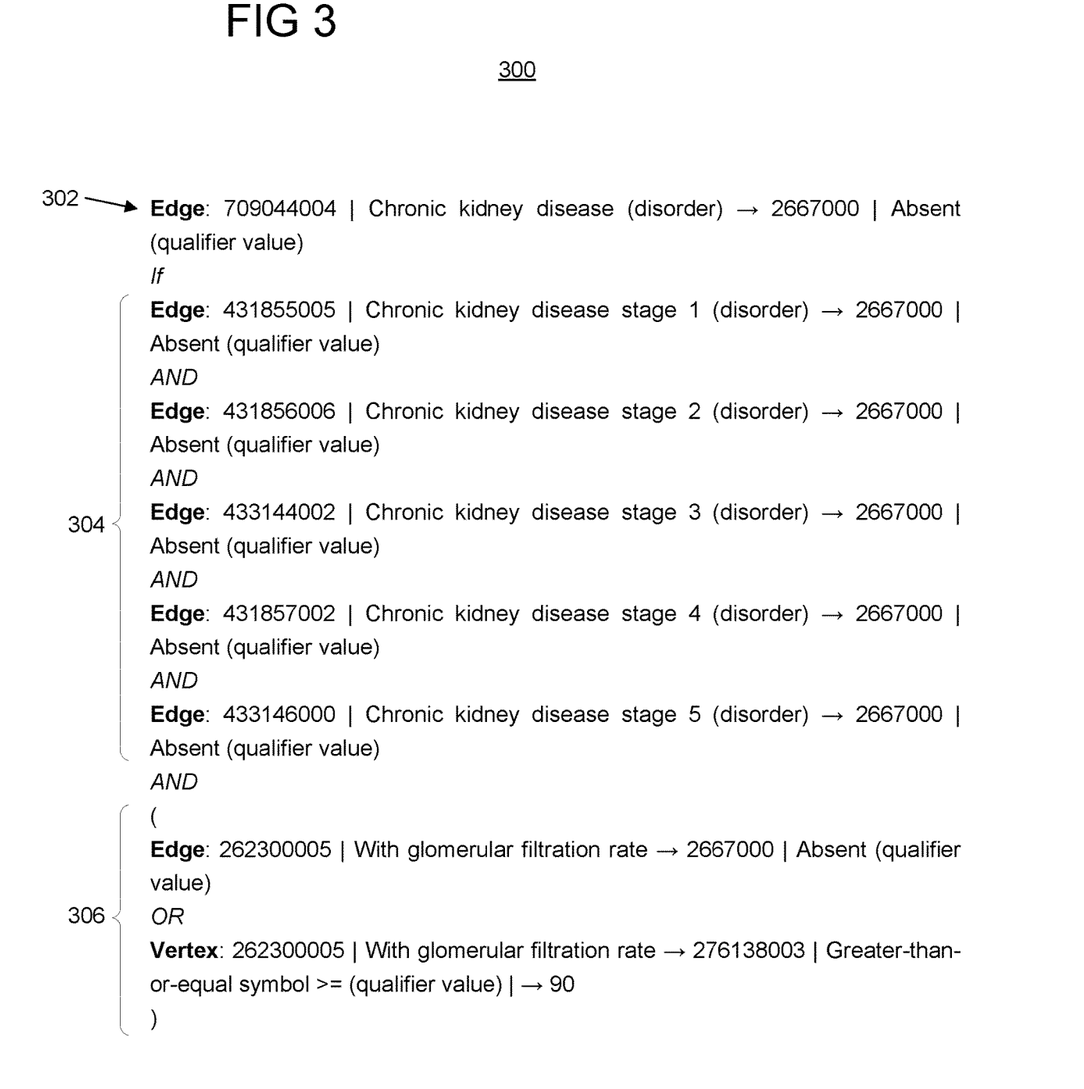
FIG. 3 shows an exemplary commit comprising equations defining edge properties and vertex properties, in accordance with one or more embodiments.

FIG. 3 shows an exemplary commit 300 comprising equations defining edge properties and vertex properties, in accordance with one or more embodiments. Commit 300 implements a rule for determining that a patient does not have chronic kidney disease in a medical ontology, which can be expressed as follows:

No Chronic Kidney Disease==(Glomerular Filtration Rate (GFR)>=90 OR GFR Not Available) AND No Positive for Chronic Kidney Stage 1 to 5

As shown in FIG. 3, equation 302 adds an edge in the medical ontology between vertex 709044004 representing chronic kidney disease and vertex 2667000 representing a property of absent to indicate no chronic kidney disease if each of equations 304 is true and at least one of equations 306 is true. Equations 304 respectively determine whether edges exist in the medical ontology between vertices representing chronic kidney disease stages 1-5 and a vertex representing a property of absent to indicate no positive for chronic kidney stages 1 to 5. Equations 306 determine whether an edge exists in the medical ontology between vertex 262300005 representing glomerular filtration rate and vertex 2667000 representing a property of value to indicate GFR not available or whether a vertex 276138003 representing a property value of greater than or equal to 90 exists in the medical ontology from vertex 262300005 representing glomerular filtration rate.

At step 206 of FIG. 2, an evaluation of the one or more patients is determined based on the user input using a medical ontology configured with the one or more retrieved commit bundles. The medical ontology is separate from the commit database. The medical ontology may be any suitable ontology, such as, e.g., a systemized nomenclature of medical (SNOMED) ontology.

In one example, as shown in guideline runtime stage 102 of FIG. 1, base ontology 108 is configured or loaded with the retrieved commit bundle 124 in memory by reference engine 110 to generate an enhanced ontology web ontology language (OWL) file 112. As shown in FIG. 1, base ontology 108 is separate from commit database 122. Enhanced ontology OWL file 112 is applied and deployed during guideline runtime stage 102 when a user query or patient data instance runs. The medical ontology defined by enhanced ontology OWL file 112 represents relationships between input data instances 114 to generate the evaluation of the one or more patients according to the user input. Input data instances 114 may comprise any suitable data for the evaluation of the one or more patients. For example, the input data instances 114 may comprise patient data (e.g., medical imaging data, lab results, patient medical history, patient demographic, etc.), acquisition protocol parameters from a scanner, metadata for lab protocols, etc.

At step 208 of FIG. 2, the evaluation of the one or more patients is output. The evaluation of the one or more patients can be output by displaying the evaluation of the one or more patients on a display device of a computer system, storing the evaluation of the one or more patients on a memory or storage of a computer system, or by transmitting the evaluation of the one or more patients to a remote computer system. In one example, as shown in guideline runtime stage 102 of FIG. 1, the evaluation of the one or more patients is output to ontology reasoner 106. In one embodiment, the evaluation of the one or more patients is output to a clinical decision support system for making a clinical decision based on the evaluation of the one or more patient. In another embodiment, the evaluation of the one or more patients is output to a downstream system (e.g., machine learning based system) for automatically performing a medical analysis task based on the evaluation of the one or more patients.

Figure 4:
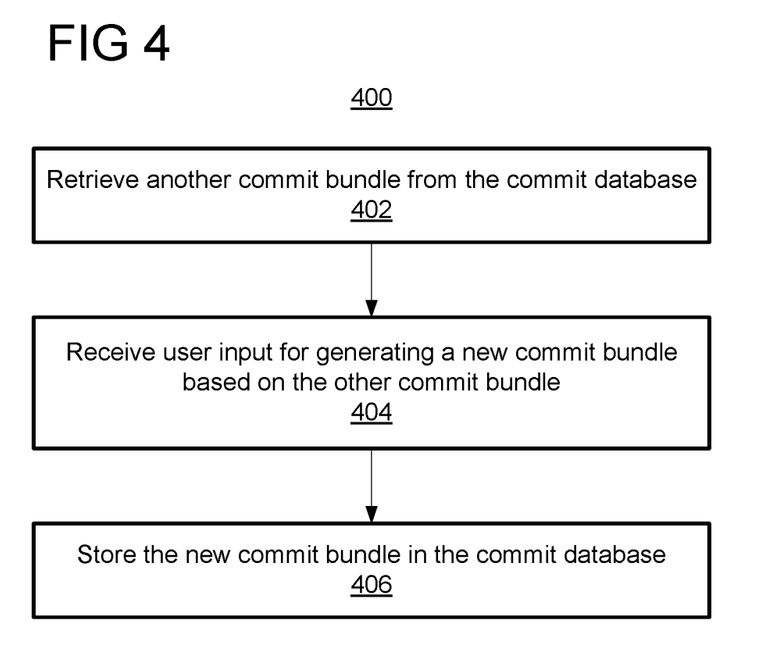
FIG. 4 shows a method for updating rules of a clinical decision tree by generating a new commit, in accordance with one or more embodiments.

FIG. 4 shows a method 400 for updating rules of a clinical decision tree by generating a new commit, in accordance with one or more embodiments. Method 400 is performed during a maintenance stage for updating the clinical decision tree, such as, e.g., end user rule maintenance stage 104 of FIG. 1. The steps of method 400 may be performed by one or more suitable computing devices, such as, e.g., computer 502 of FIG. 5.

At step 402 of FIG. 4, another commit bundle is retrieved from the commit database. The other commit bundle may be the same or different from the commit bundle retrieved at step 204 of FIG. 2. In one example, as shown in end user rule maintenance stage 104 of FIG. 1, a user may select a branch 126 in commit database 122 via user interface 120 and, in response, commit bundles 126 of the selected branch 126 are retrieved by reference engine 110, the retrieved commit bundles 124 are encoded to a user interface (UI) language by encoder 118, and the retrieved commit bundles 124 are displayed in the UI language to the user via user interface 120.

At step 404 of FIG. 4, user input is received for generating a new commit bundle based on the other commit bundle. In one example, as shown in end user rule maintenance stage 104 of FIG. 1, the user can view the retrieved commit bundles for one or more timestamps for a branch 126 representing different versions of the clinical decision tree. A new commit can be created based on a selected one of the retrieved commit bundles 124 by adding to, removing from, and/or modifying the edge properties and/or vertex properties of the selected retrieved commit bundle 124. In one embodiment, the new commit is created by creating new edges between two vertices, deleting existing edges, changing property values in existing commits, etc. A new commit bundle comprising the new commit and associated provenance metadata is thus generated.

In one example, to change a GFR threshold value from 90 to 80 in commit 300 of FIG. 3, the user selects a prior commit 124 and changes the value of the GFT threshold from 90 to 80 via user interface 120. During guideline runtime stage 102 (as described above with respect to FIG. 2) for evaluating one or more patients, reference engine 110 will retrieve the new commit for chronic kidney disease estimation from commit database 122.

At step 406 of FIG. 4, the new commit bundle is stored in the commit database. In one example, as shown in end user rule maintenance stage 104 of FIG. 1, the new commit bundle is stored in memory in commit database 122.

Advantageously, embodiments described herein improve upon existing medical ontological systems by enabling non-expert, non-developer end users to update the commits representing rules of the clinical decision trees to thereby provide for scalable and maintainable clinical decision trees. As used herein, a non-developer end user refers to a user who is not qualified as a software developer.

In one embodiment, commit database 122 of FIG. 1 may be configured to include custom access controls for different branches 126, versions of commit bundles 124, graphical edge adders, etc. to make the clinical decision trees more scalable and easier for the end user at clinical sites to maintain.

In one embodiment, a plurality of users may update commit bundles 124 in parallel.

In one embodiment, a notification may be transmitted to the user prior to deployment of updated commit bundles 124 to alert the user of potential errors or inconsistencies in results.

In one embodiment, the updated commit bundles may be tested with synthetic patient data prior to deployment in production. The synthetic patient data can be adapted to broadly cover the entire range of scenarios that may be encountered.

In one embodiment, commits from a plurality of clinical sites can be merged in a transparent and end user controller manner.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system. Similarly, features described herein with respect to one embodiment can be applied to other embodiments described herein.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-2 and 4. Certain steps or functions of the methods and workflows described herein, including one or more of the steps or functions of FIGS. 1-2 and 4, may be performed by a server or by another processor in a network-based cloud-computing system. Certain steps or functions of the methods and workflows described herein, including one or more of the steps of FIGS. 1-2 and 4, may be performed by a client computer in a network-based cloud computing system. The steps or functions of the methods and workflows described herein, including one or more of the steps of FIGS. 1-2 and 4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-2 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
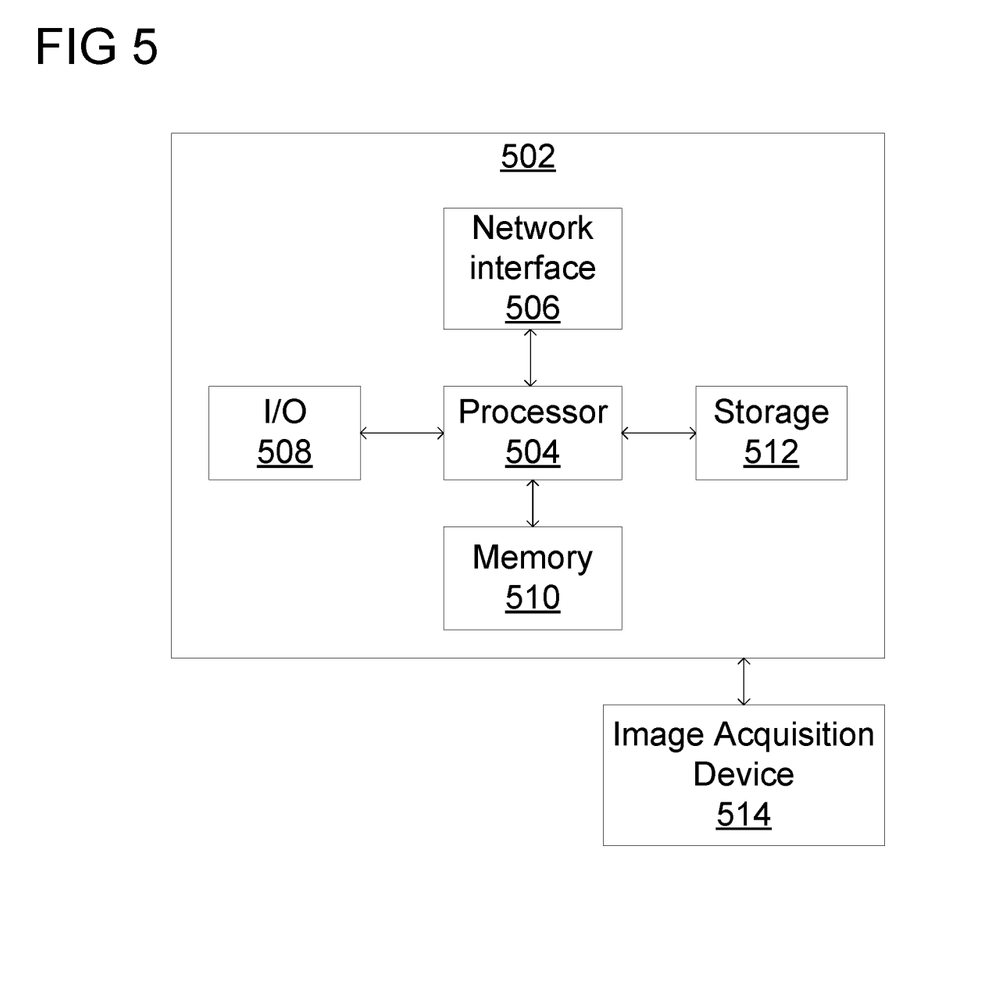
FIG. 5 shows a high-level block diagram of a computer that may be used to implement one or more embodiments.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIGS. 1-2 and 4 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIGS. 1-2 and 4. Accordingly, by executing the computer program instructions, the processor 504 executes the method and workflow steps or functions of FIGS. 1-2 and 4. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. Image acquisition device 514 may be any clinical decision tree consumer image acquisition device for protocol selection, clinical decision support systems, clinical workflow systems, etc. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

Any or all of the systems and apparatus discussed herein may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:
1. A computer-implemented method comprising:
receiving user input for evaluating one or more patients;
retrieving a commit bundle from a commit database, the commit bundle comprising a commit representing rules of a decision tree, the commit comprising a set of equations of edge properties and/or vertex properties;

determining an evaluation of the one or more patients based on the user input using a medical ontology configured with the retrieved commit bundle, the medical ontology being separate from the commit database; and outputting results of the evaluation of the one or more patients.

2. The computer-implemented method of claim 1, further comprising:

retrieving another commit bundle from the commit database;

receiving user input for generating a new commit bundle based on the other commit bundle; and storing the new commit bundle in the commit database.

3. The computer-implemented method of claim 2, wherein the user input for generating the new commit bundle is received from a non-developer end user.

4. The computer-implemented method of claim 1, wherein the commit database comprises a plurality of commit bundles representing different versions of rules of a decision tree.

5. The computer-implemented method of claim 1, wherein the commit bundle comprises provenance metadata associated with the commit.

6. The computer-implemented method of claim 1, wherein the set of equations of edge properties and/or vertex properties define modifications relative to a prior commit of a prior commit bundle.

7. The computer-implemented method of claim 1, wherein the set of equations of edge properties are based on a presence or absence of one or more edges in the medical ontology.

8. The computer-implemented method of claim 1, wherein the set of equations of vertex properties are based on values of properties associated with one or more vertices.

9. An apparatus comprising:

means for receiving user input for evaluating one or more patients;

means for retrieving a commit bundle from a commit database, the commit bundle comprising a commit representing rules of a decision tree, the commit comprising a set of equations of edge properties and/or vertex properties;

means for determining an evaluation of the one or more patients based on the user input using a medical ontology configured with the retrieved commit bundle, the medical ontology being separate from the commit database; and means for outputting results of the evaluation of the one or more patients.

10. The apparatus of claim 9, wherein the commit bundle comprises provenance metadata associated with the commit.

11. The apparatus of claim 9, wherein the set of equations of edge properties and/or vertex properties define modifications relative to a prior commit of a prior commit bundle.

12. The apparatus of claim 9, wherein the set of equations of edge properties are based on a presence or absence of one or more edges in the medical ontology.

13. The apparatus of claim 9, wherein the set of equations of vertex properties are based on values of properties associated with one or more vertices.

14. A non-transitory computer readable medium storing computer program instructions, the computer program instructions when executed by a processor cause the processor to perform operations comprising:

receiving user input for evaluating one or more patients;

retrieving a commit bundle from a commit database, the commit bundle comprising a commit representing rules of a decision tree, the commit comprising a set of equations of edge properties and/or vertex properties;

determining an evaluation of the one or more patients based on the user input using a medical ontology configured with the retrieved commit bundle, the medical ontology being separate from the commit database; and outputting results of the evaluation of the one or more patients.

15. The non-transitory computer readable medium of claim 14, the operations further comprising:

retrieving another commit bundle from the commit database;

receiving user input for generating a new commit bundle based on the other commit bundle; and storing the new commit bundle in the commit database.

16. The non-transitory computer readable medium of claim 14, wherein the commit database comprises a plurality of commit bundles representing different versions of rules of a decision tree.

17. The non-transitory computer readable medium of claim 14, wherein the commit bundle comprises provenance metadata associated with the commit.

18. The non-transitory computer readable medium of claim 14, wherein the set of equations of edge properties and/or vertex properties define modifications relative to a prior commit of a prior commit bundle.

19. The non-transitory computer readable medium of claim 14, wherein the set of equations of edge properties are based on a presence or absence of one or more edges in the medical ontology.

20. The non-transitory computer readable medium of claim 14, wherein the set of equations of vertex properties are based on values of properties associated with one or more vertices.

* * * * *